United States Patent
Chou et al.

(10) Patent No.: US 7,872,741 B2
(45) Date of Patent: Jan. 18, 2011

(54) METHOD AND APPARATUS FOR SCATTERFIELD MICROSCOPICAL MEASUREMENT

(75) Inventors: Sen-Yih Chou, Taipei (TW); Shu-Ping Dong, Taichung County (TW); Wei-Te Hsu, Taipei County (TW); Deh-Ming Shyu, Miaoli County (TW); Chia-Lin Wu, Hsinchu (TW); Yi-Sha Ku, Hsinchu (TW); Chang-Hai Sung, Hsinchu County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 61 days.

(21) Appl. No.: 12/071,362

(22) Filed: Feb. 20, 2008

(65) Prior Publication Data

US 2009/0079969 A1 Mar. 26, 2009

(30) Foreign Application Priority Data

Sep. 21, 2007 (TW) .............................. 96135264 A

(51) Int. Cl.
*G01N 21/00* (2006.01)
(52) U.S. Cl. .............. 356/237.1; 356/237.2; 356/237.5; 356/497; 359/235; 359/368
(58) Field of Classification Search ................. 356/445, 356/497, 237.1; 250/492.1, 201.3; 355/67, 355/43, 77
See application file for complete search history.

(56) References Cited

U.S. PATENT DOCUMENTS

| | | | | |
|---|---|---|---|---|
| 6,133,986 A * | 10/2000 | Johnson | ....................... | 355/67 |
| 6,392,752 B1 * | 5/2002 | Johnson | ....................... | 356/511 |
| 6,934,079 B2 * | 8/2005 | Hell et al. | ................... | 359/368 |
| 7,061,623 B2 | 6/2006 | Davidson | | |
| 7,545,505 B2 * | 6/2009 | Lehmann et al. | ............ | 356/497 |
| 2003/0021016 A1 * | 1/2003 | Grier | ......................... | 359/368 |

(Continued)

OTHER PUBLICATIONS

"Scatterfield Microscopy Using Back Focal Plane Imaging with an Engineered Illumination Field," Proc. of SPIE, vol. 6152. 61520J (2006) by H. J. Patrick, R. Atota, B. M. Barnes, et al., with National Institute of Standards and Technology (NIST).

*Primary Examiner*—Tarifur R. Chowdhury
*Assistant Examiner*—Isiaka O Akanbi
(74) *Attorney, Agent, or Firm*—Birch, Stewart, Kolasch & Birch, LLP

(57) ABSTRACT

A method and an apparatus are disclosed for scatterfield microscopical measurement. The method integrates a scatterometer and a bright-field microscope for enabling the measurement precision to be better than the optical diffraction limit. With the aforesaid method and apparatus, a detection beam is generated by performing a process on a uniform light using an LCoS (liquid crystal on silicon) or a DMD (digital micro-mirror device) which is to directed to image on the back focal plane of an object to be measured, and then scattered beams resulting from the detection beam on the object's surface are focused on a plane to form an optical signal which is to be detected by an array-type detection device. The detection beam can be oriented by the modulation device to illuminate on the object at a number of different angles, by which zero order or higher order diffraction intensities at different positions of the plane at different incident angles can be collected.

2 Claims, 6 Drawing Sheets

U.S. PATENT DOCUMENTS

2004/0174593 A1* 9/2004 Weyh et al. .................. 359/388
2007/0035734 A1* 2/2007 Muller et al. ............... 356/432
2007/0051869 A1* 3/2007 Knebel .................... 250/201.3
2008/0037114 A1* 2/2008 Sheblee et al. .............. 359/385

* cited by examiner

METHOD AND APPARATUS FOR SCATTERFIELD MICROSCOPICAL MEASUREMENT

BACKGROUND OF THE INVENTION

1. Field of the Invention

The present invention generally relates to a method and an apparatus for microscopical measurement and, more particularly, to a method and an apparatus for surface structure measurement, integrating a scatterometer and a bright-field microscope.

2. Description of the Prior Art

With the rapid development in semiconductor processing, the feature size has advanced to 65 nm, which is smaller than the optical diffraction limit. Therefore, conventional optical microscopes are insufficient to form clear images to meet the requirements for advanced semiconductor processing.

As disclosed in "Scatterfield Microscopy Using Back Focal Plane Imaging with an Engineered Illumination Field," Proc. Of SPIE, vol. 6152. 61520J (2006) by H. J. Patrick, R. Atota, B. M. Barnes, et al. with National Institute of Standards and Technology (NIST), bright-field microscopy is used as shown in FIG. 1. The image of a mask 11 is formed on the back focal plane 14 of an objective lens 13 using a relay system 12. The incident angle is changed according to the movement of the mask 11. A charge-coupled device (CCD) camera 15 is used to record the diffracted light at different incident angles. Even though such a structure is simpler than the conventional scatterometer, precision control for the movement of the mask is required.

In U.S. Pat. No. 7,061,623 B2, an interference microscope is used as shown in FIG. 2. The sample position or the reference plane is varied to select the incident light illuminating on the sample while the rest of light does not illuminate on the sample due to destructive interference. This patent is inventive in that an interference microscope is used to select the incident light according to the incident angle and to record the reflected light corresponding to specific incident angles. However, with such an interference microscope, precise position control is still required so as to select the incident light. Moreover, the use of an interference microscope makes system modeling more complicated and surface analysis more difficult.

SUMMARY OF THE INVENTION

It is a primary object of the present invention to provide a method and an apparatus for scatterfield microscopical measurement, using an optical switching array device to control the incident light illuminating on a sample at different incident angles to prevent inaccuracy due to mechanical actuation. Therefore, the apparatus of the present invention is simplified, more reliable and easier to be integrated with other equipments.

In one embodiment, the present invention provides a method for scatterfield microscopical measurement, comprising steps of:

generating a detection beam by performing a process on a uniform light using a switching array;

forming an optical signal by projecting the detection beam through an microscopical objective lens to image on a back focal plane of the microscopical objective lens and focusing zero or higher order diffraction beams resulting from the detection beam illuminating on an object under test; and acquiring the optical signal by an array-type detection device.

In one embodiment, the present invention provides an apparatus for scatterfield microscopical measurement, comprising:

a light source module, capable of providing a uniform light;

an optical switching array device, capable of adjusting the intensity of the uniform light to generate a detection beam;

a beam splitting unit, disposed between the light source module and the optical switching array device to introduce the uniform light into the optical switching array device and to allow the detection beam to pass through;

an objective lens set with a back focal plane, capable of generating an optical signal by projecting the detection beam passing through the beam splitting unit onto an object under test to generate a scattered light and focus the scattered light on the back focal plane; and an array-type detection device, capable of acquiring the optical signal.

In another embodiment, the present invention provides an apparatus for scatterfield microscopical measurement, comprising:

a light source module, capable of providing a uniform light;

an optical switching array device, capable of adjusting the position where the uniform light passes through to generate a detection beam;

an objective lens set with a back focal plane, capable of generating an optical signal by projecting the detection beam passing through the objective lens set onto an object under test to generate a scattered light and focus the scattered light on the back focal plane; and an array-type detection device, capable of acquiring the optical signal.

BRIEF DESCRIPTION OF THE DRAWINGS

The objects, spirits and advantages of the preferred embodiments of the present invention will be readily understood by the accompanying drawings and detailed descriptions, wherein.

DETAILED DESCRIPTION OF THE PREFERRED EMBODIMENT

Figure 1:
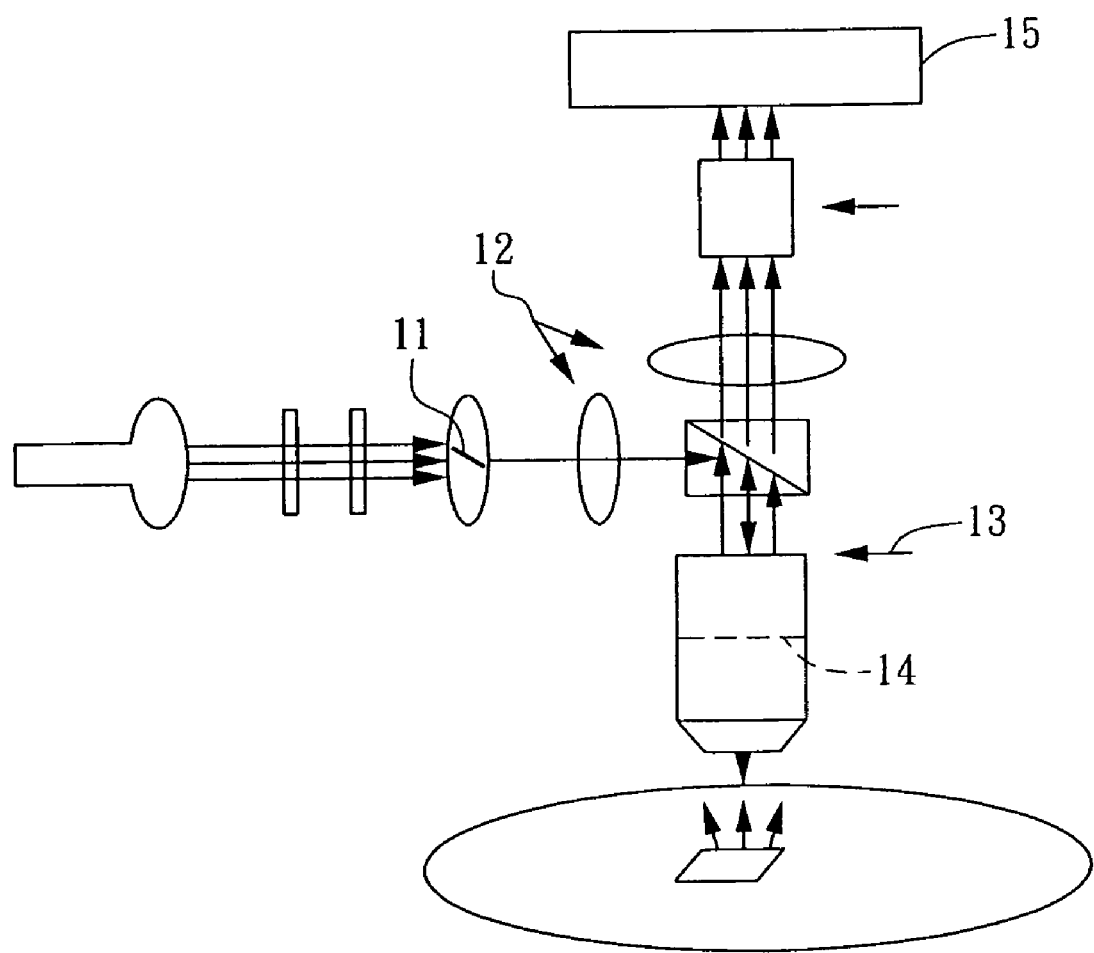
FIG. 1 is a schematic diagram showing a conventional apparatus for scatterfield microscopical measurement.
Figure 2:
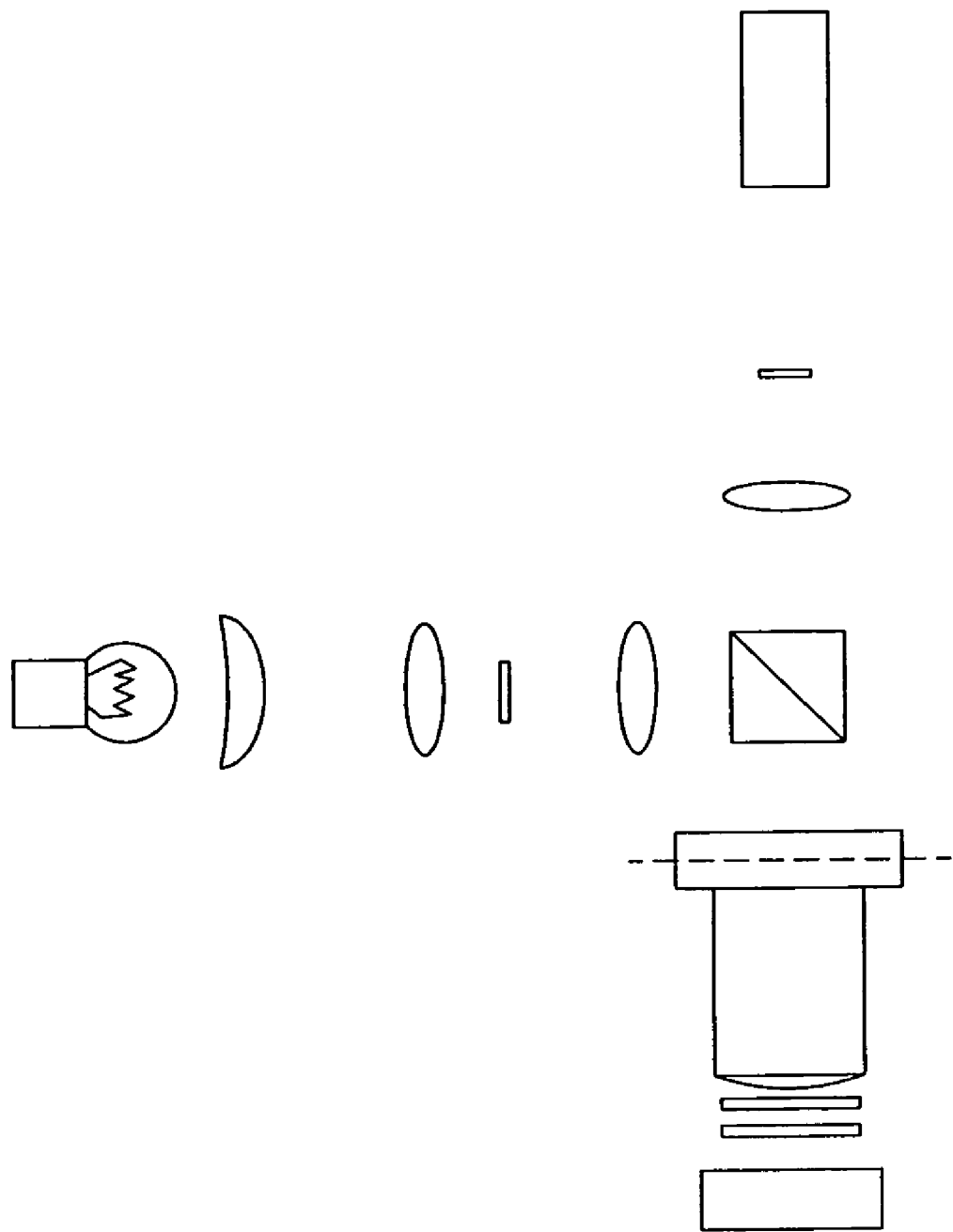
FIG. 2 is a schematic diagram showing another conventional apparatus for scatterfield microscopical measurement.
Figure 3:
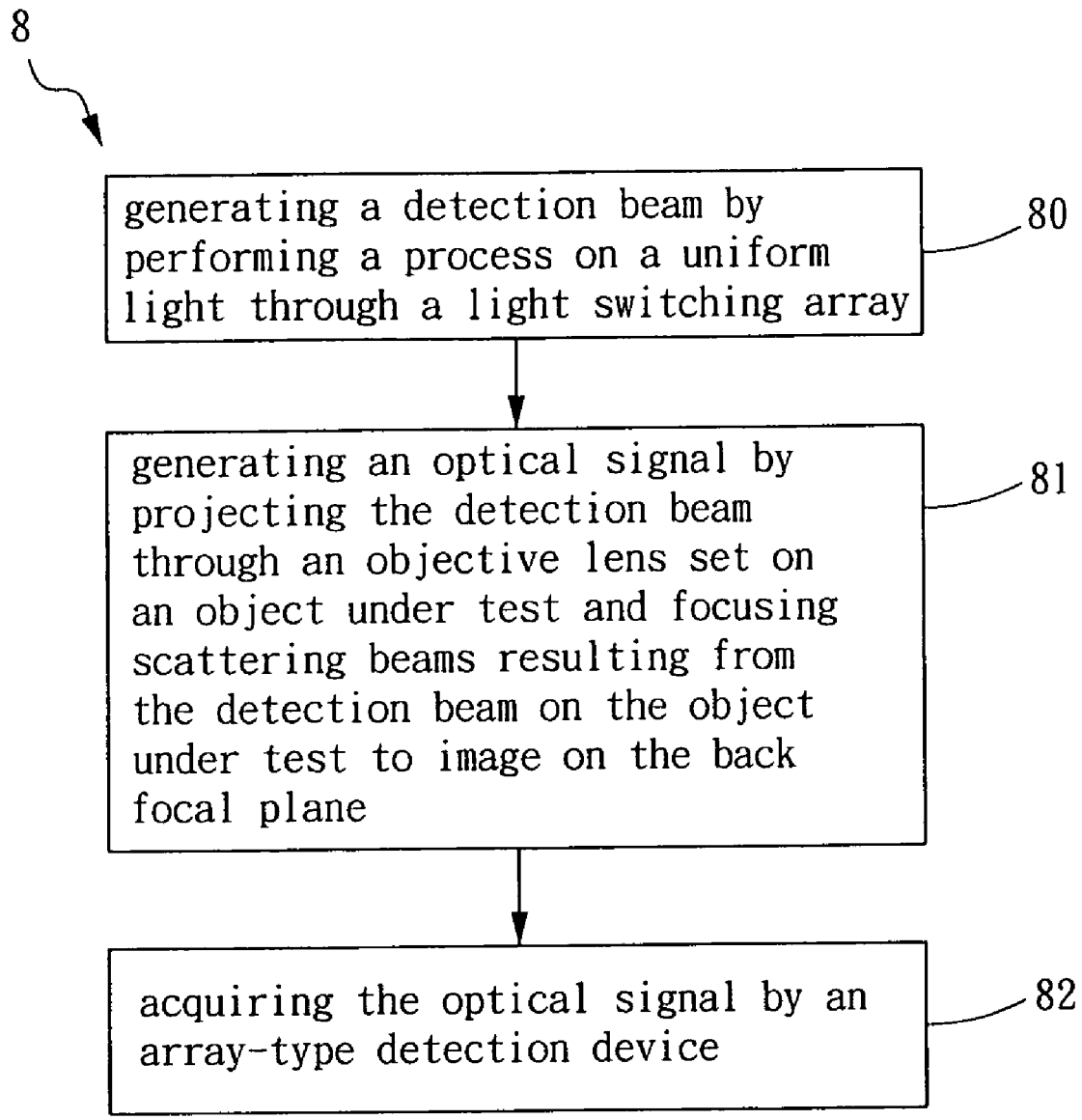
FIG. 3 is a flow-chart of a method for scatterfield microscopical measurement according to the present invention.

Please refer to FIG. 3, which is a flow-chart of a method for scatterfield microscopical measurement according to the present invention. In the method 8, Step 80 is performed to generate a detection beam by performing a process on a uniform light through an optical switching array device. Then in Step 81, an optical signal is formed by projecting the detection beam through an objective lens set on an object under test and focusing scattering beams resulting from the detection beam on the object under test to image on the back focal plane. Finally, the optical signal is acquired by an array-type detection device in Step 82.

To implement the aforementioned method, the present invention can be exemplified by the preferred embodiments as described hereinafter. However, it is noted that the embodiments are only exemplary and the present invention is not limited thereto.

First Embodiment

Figure 4:
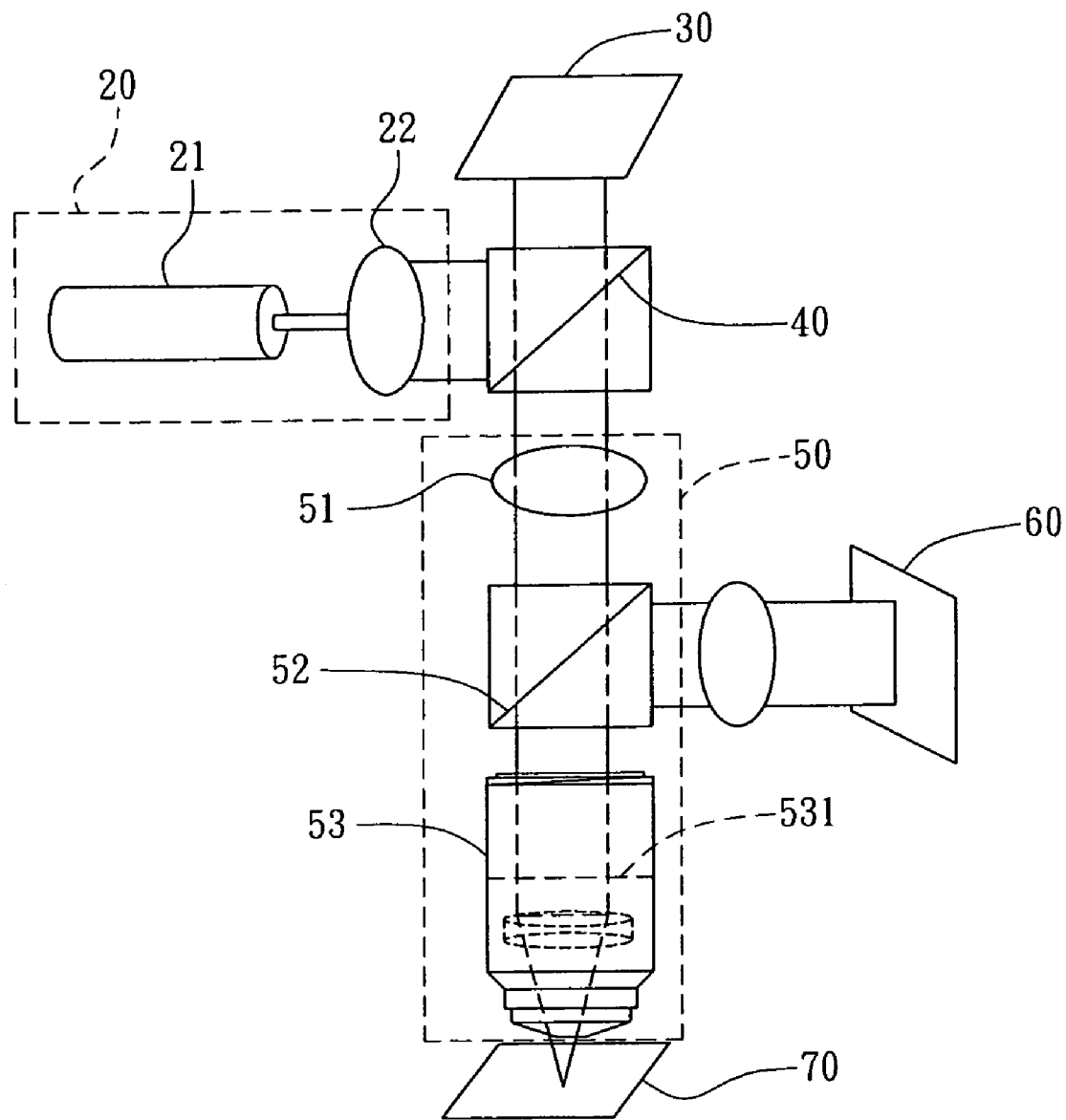
FIG. 4 is a schematic diagram showing an apparatus for scatterfield microscopical measurement according to a first embodiment of the present invention.

Please refer to FIG. 4, which is a schematic diagram showing an apparatus for scatterfield microscopical measurement according to a first embodiment of the present invention. In the first embodiment, the apparatus comprises a light source module 20, an optical switching array device 30, a beam splitting unit 40, an objective lens set 50 and an array-type detection device 60. The light source module 40 is capable of providing a uniform light. The light source module 40 comprises a light source 21 and a beam expander 22. The light source 21 is capable of providing a light beam. In the present embodiment, the light source is exemplified by but not limited to a laser, an LED or a white light source. The beam expander 22 is capable of expanding the light beam into a uniform light. The optical switching array device 30 is an array-type switching device such as a liquid crystal on silicon (LCoS) device or a digital micro-mirror device (DMD). The optical switching array device 30 is signal-controlled to reflect the uniform light to generate the detection beam.

The beam splitting unit 40 is disposed between the light source module 20 and the optical switching array device 30 to introduce the uniform light into the optical switching array device 30 and to allow the detection beam to pass through.

Figure 5:
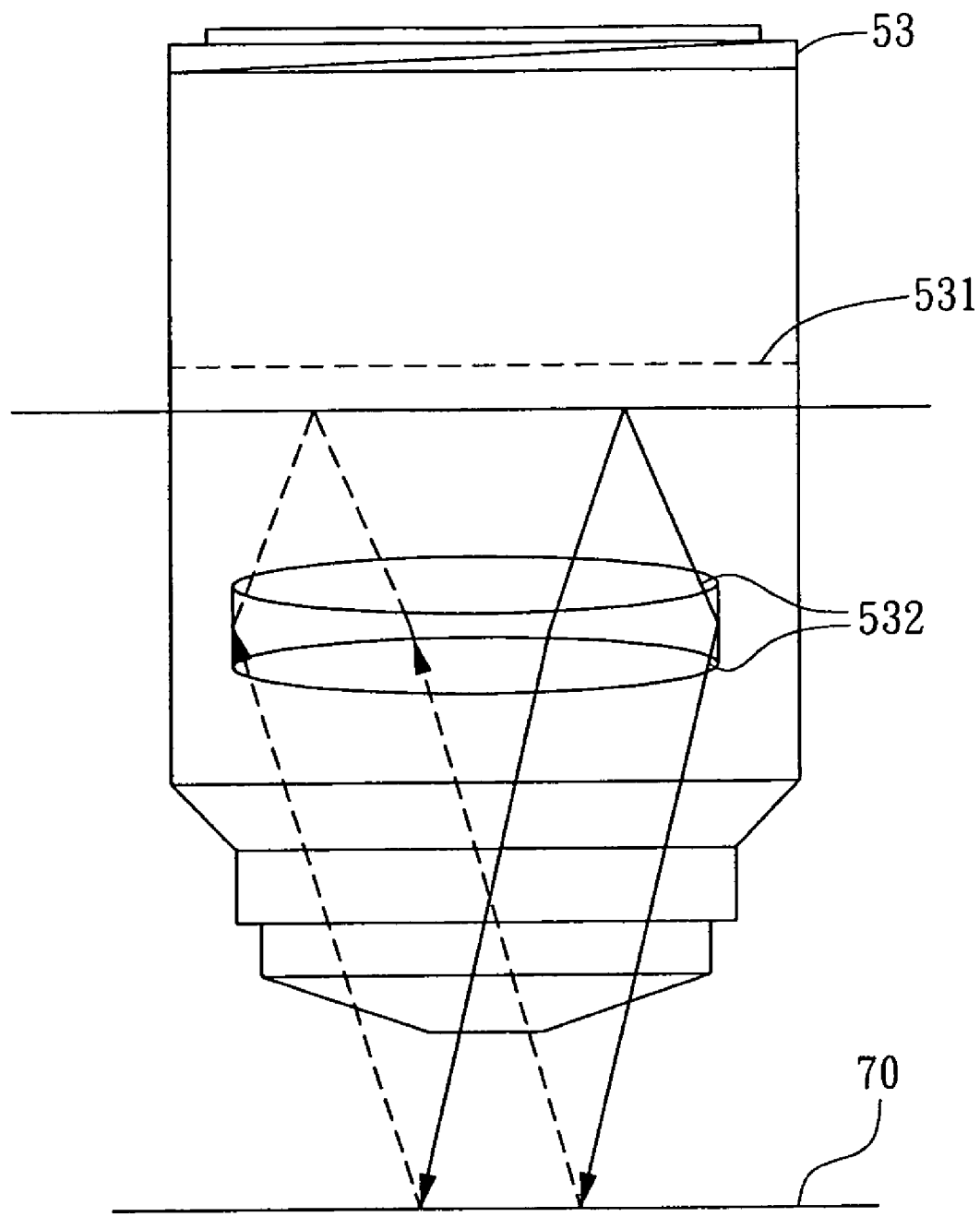
FIG. 5 is schematic diagram showing that an image is formed on the back focal plane by a scattered light.

The detection beam passes through the beam splitting unit 40 to enter the objective lens set 50. The objective lens set 50 comprises a relay lens 51, a beam splitter 52 and a microscopical objective lens 53. The microscopical objective lens 53 has a back focal plane 531. The detection beam passing through the beam splitting unit 40 is projected onto an object under test 70 to generate a scattered light to be focused on the back focal plane 531 to generate an optical signal, as shown in FIG. 5. The incident light illuminating on the back focal plane 531 becomes a planar wave incident on the object under test 70 after passing through an objective lens set 532. The scattered light from the object under test 70 is focused on the back focal plane 531 to form an optical signal. The optical signal is acquired by an array-type detection device 60. The array-type detection device 60 is a CCD (charge-coupled device) or a CMOS (complimentary metal oxide semiconductor) device. However, the present invention is not limited thereto.

Second Embodiment

Figure 6:
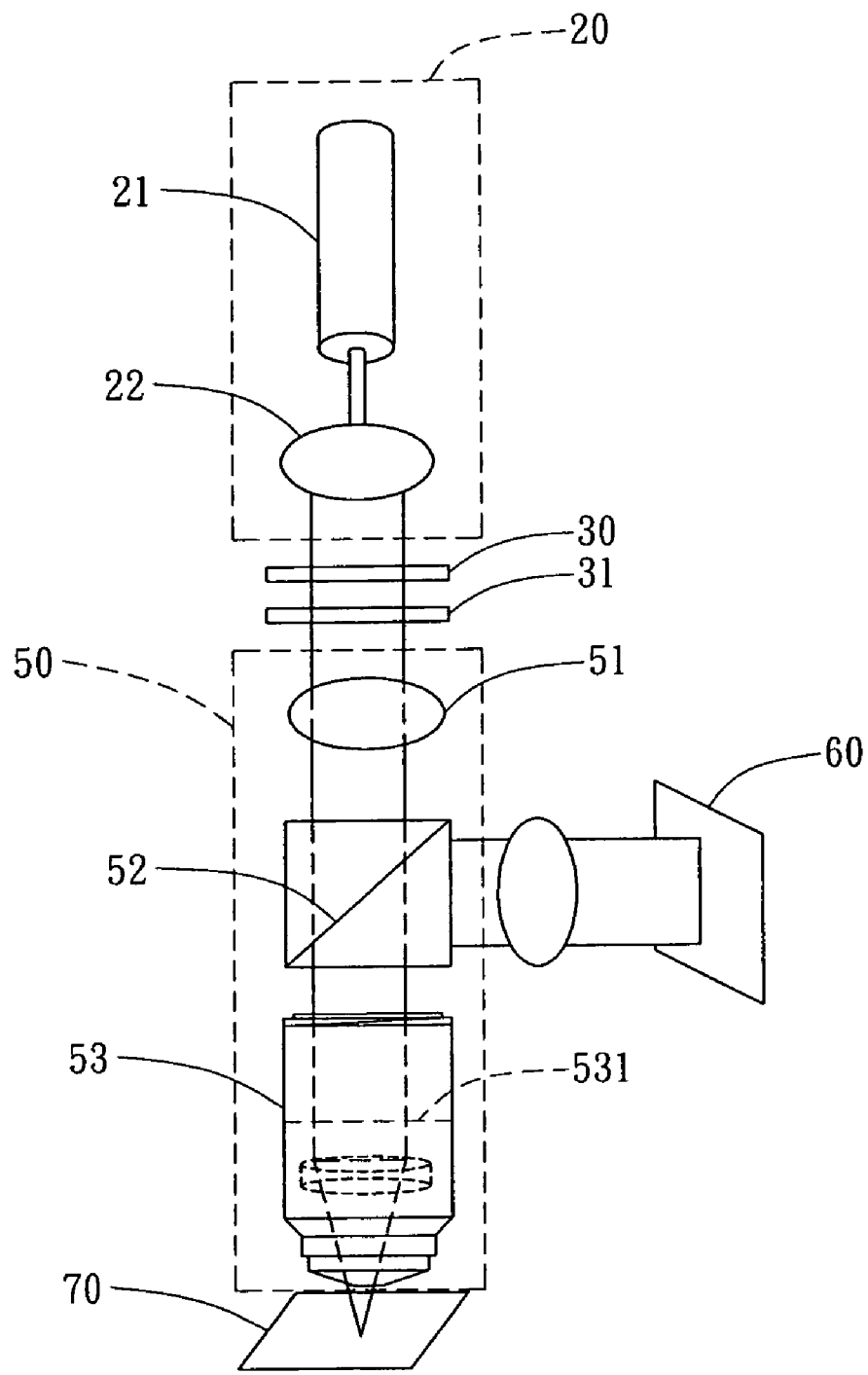
FIG. 6 is a schematic diagram showing an apparatus for scatterfield microscopical measurement according to a second embodiment of the present invention.

Please refer to FIG. 6, which is a schematic diagram showing an apparatus for scatterfield microscopical measurement according to a second embodiment of the present invention. In the second embodiment, the apparatus comprises a light source module 20, an optical switching array device 30, an objective lens set 50 and an array-type detection device 60. The light source module 40 is capable of providing a uniform light. The light source module 40 comprises a light source 21 and a beam expander 22. The light source 21 is capable of providing a light beam. In the present embodiment, the light source is exemplified by but not limited to a laser, an LED or a white light source. The beam expander 22 is capable of expanding the light beam into a uniform light. The optical switching array device 30 is an array-type switching device such as a liquid crystal on silicon (LCoS) device. The optical switching array device 30 is signal-controlled so that the uniform light passes through the switching array to generate the detection beam.

The detection beam passes through the optical switching array device 30 and a polarizing beam splitter 31 to enter the objective lens set 50. The objective lens set 50 comprises a relay lens 51, a beam splitter 52 and a microscopical objective lens 53. The microscopical objective lens 53 has a back focal plane 531. The detection beam is projected onto an object under test 70 to generate a scattered light to be focused on the back focal plane 531 to generate an optical signal, as shown in FIG. 4. The optical signal is acquired by an array-type detection device 60. The array-type detection device 60 is a CCD (charge-coupled device) or a CMOS (complimentary metal oxide semiconductor) device.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. An apparatus for scatterfield microscopical measurement, comprising:
   a light source module, capable of providing a uniform light;
   an optical switching array device, capable of adjusting the intensity of the uniform light to generate a detection beam, wherein the optical switching array device is an LCoS (liquid crystal on silicon) device or a DMD (digital micro-mirror device);
   a beam splitting unit, disposed between the light source module and the optical switching array device to introduce the uniform light into the optical switching array device and to allow the detection beam to pass through;
   an objective lens comprising a relay lens, a beam splitter and a microscopical objective lens which set with a back focal plane, the objective lens being capable of generating an optical signal by projecting the detection beam passing through the beam splitting unit onto an object under test to generate a scattered light and focus the scattered light on the back focal plane; and
   an array-type detection device capable of acquiring the optical signal and disposed corresponding to the beam splitter of the objective lens, wherein the array-type detection device is a CCD (charge-coupled device) or a CMOS (complimentary metal oxide semiconductor) device.

2. An apparatus for scatterfield microscopical measurement, comprising:
   a light source module, capable of providing a uniform light;
   an optical switching array device, capable of adjusting the position where the uniform light passes through to generate a detection beam, wherein the optical switching array device is an LCoS (liquid crystal on silicon) device or a DMD (digital micro-mirror device);
   a beam splitting unit, disposed between the light source module and the optical switching array device to introduce the uniform light into the optical switching array device and to allow the detection beam to pass through;
   an objective lens comprising a relay lens, a beam splitter and a microscopical objective lens which set with a back focal plane, the objective lens being capable of generating an optical signal by projecting the detection beam passing through the objective lens set onto an object under test to generate a scattered light and focus the scattered light on the back focal plane; and an array-type detection device capable of acquiring the optical signal and disposed corresponding to the beam splitter of the objective lens, wherein the array-type detection device is a CCD (charge-coupled device) or a CMOS (complimentary metal oxide semiconductor) device.

* * * * *